United States Patent
Utsumi et al.

(10) Patent No.: US 9,116,096 B2
(45) Date of Patent: Aug. 25, 2015

(54) MULTI-RADIATION UNIT AND RADIATION IMAGING SYSTEM INCLUDING THE UNIT

(71) Applicant: CANON KABUSHIKI KAISHA, Tokyo (JP)

(72) Inventors: Kazushige Utsumi, Sagamihara (JP); Kazuya Tsujino, Tokyo (JP); Kazuyuki Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 120 days.

(21) Appl. No.: 14/076,528

(22) Filed: Nov. 11, 2013

(65) Prior Publication Data
US 2014/0133628 A1 May 15, 2014

(30) Foreign Application Priority Data
Nov. 13, 2012 (JP) ................................ 2012-248965

(51) Int. Cl.
*G01N 23/04* (2006.01)
*H05G 1/70* (2006.01)

(52) U.S. Cl.
CPC ............... *G01N 23/04* (2013.01); *H05G 1/70* (2013.01); *G01N 2223/204* (2013.01); *H01J 2235/186* (2013.01)

(58) Field of Classification Search
USPC .......................................... 378/124, 134, 138
See application file for complete search history.

(56) References Cited

U.S. PATENT DOCUMENTS

| 7,873,146 B2 | 1/2011 | Okunuki et al. |
| 7,991,120 B2 | 8/2011 | Okunuki et al. |
| 2007/0188091 A1* | 8/2007 | Kimiya et al. ................ 313/506 |
| 2012/0140895 A1* | 6/2012 | Okunuki et al. .............. 378/122 |

FOREIGN PATENT DOCUMENTS

| JP | 2007265981 A | 10/2007 |
| JP | 2012038475 A | 2/2012 |

* cited by examiner

*Primary Examiner* — Kiet T Nguyen
(74) *Attorney, Agent, or Firm* — Canon USA Inc. IP Division (57) ABSTRACT

A multi-radiation unit includes: a multi-radiation tube which has a plurality of electron sources, a plurality of targets and an intermediate electrode having openings through which electrons emitted from the electron sources pass; a selection circuit that allows electrons to be emitted from a selected electron source selected from the plurality of electron sources; an intermediate electrode potential defining unit that defines a potential of the intermediate electrode; a storage unit that stores, for each of the plurality of electron sources, an electrostatic control condition of the intermediate electrode for obtaining a predetermined irradiated state of a target corresponding to the selected electron source; and a changing unit that changes, when electrons are emitted from the selected electron source, the electrostatic control condition of the intermediate electrode based on the electrostatic control condition stored in the storage unit for the selected electron source.

7 Claims, 9 Drawing Sheets

MULTI-RADIATION UNIT AND RADIATION IMAGING SYSTEM INCLUDING THE UNIT

BACKGROUND

1. Field of the Invention

The present invention generally relates to radiation imaging, and more particularly it relates to a multi-radiation unit and a radiation imaging system using the unit. These can be applicable to radiation imaging for medical diagnosis or non-destructive inspection in the fields of medical and industrial equipment.

2. Description of Related Art

A radiation tube generally accelerates electrons emitted from an electron source to have high energy to form an electron beam having a desired shape, and then a target is irradiated with the electron beam to generate radiation from the target.

Japanese Patent Application Laid-Open No. 2007-265981 discloses a multi-radiation tube in which a plurality of electron sources are arranged to face a plurality of targets, respectively so that a plurality of radiations are generated.

The radiations generated in the multi-radiation tube have their respective intensity distributions, and each of the intensity distributions depends on the size of the focal point of the corresponding radiation. The size of the focal point of each radiation depends on the characteristic of the corresponding electron source. If the electron sources have different characteristics, the respective radiations emitted from the electron sources have different intensity distributions. Therefore, if such a multi-radiation tube is used for a radiation imaging system, for example, the quality of an entire image, such contrast of a captured image, is degraded.

SUMMARY

The present invention has been made in view of the above disadvantage and aims to achieve uniformity in the intensity distributions of a plurality of radiations generated in a multi-radiation tube.

In accordance with at least one embodiment, a multi-radiation unit includes: a multi-radiation tube which has a plurality of electron sources, a plurality of targets respectively corresponding to the plurality of electron sources and an intermediate electrode located between the electron sources and the targets, and having openings through which electrons emitted from the electron sources pass; a selection circuit configured to allow electrons to be emitted from a selected electron source selected from the plurality of electron sources; an intermediate electrode potential defining unit configured to define the potential of the intermediate electrode; a storage unit configured to store, for each of the electron sources, an electrostatic control condition of the intermediate electrode for obtaining a predetermined irradiated state of a target corresponding to the selected electron source; and a changing unit configured to change, when electrons are emitted from the selected electron source, the electrostatic control condition of the intermediate electrode based on the electrostatic control condition stored in the storage unit for the selected electron source.

Further features of the present invention will become apparent from the following description of exemplary embodiments (with reference to the attached drawings).

DESCRIPTION OF THE EMBODIMENTS

Embodiments of the present invention will be described below. In the drawings to be referred to, all like numbered elements are structurally similar and perform similar functions.

First Embodiment

Figure 1:
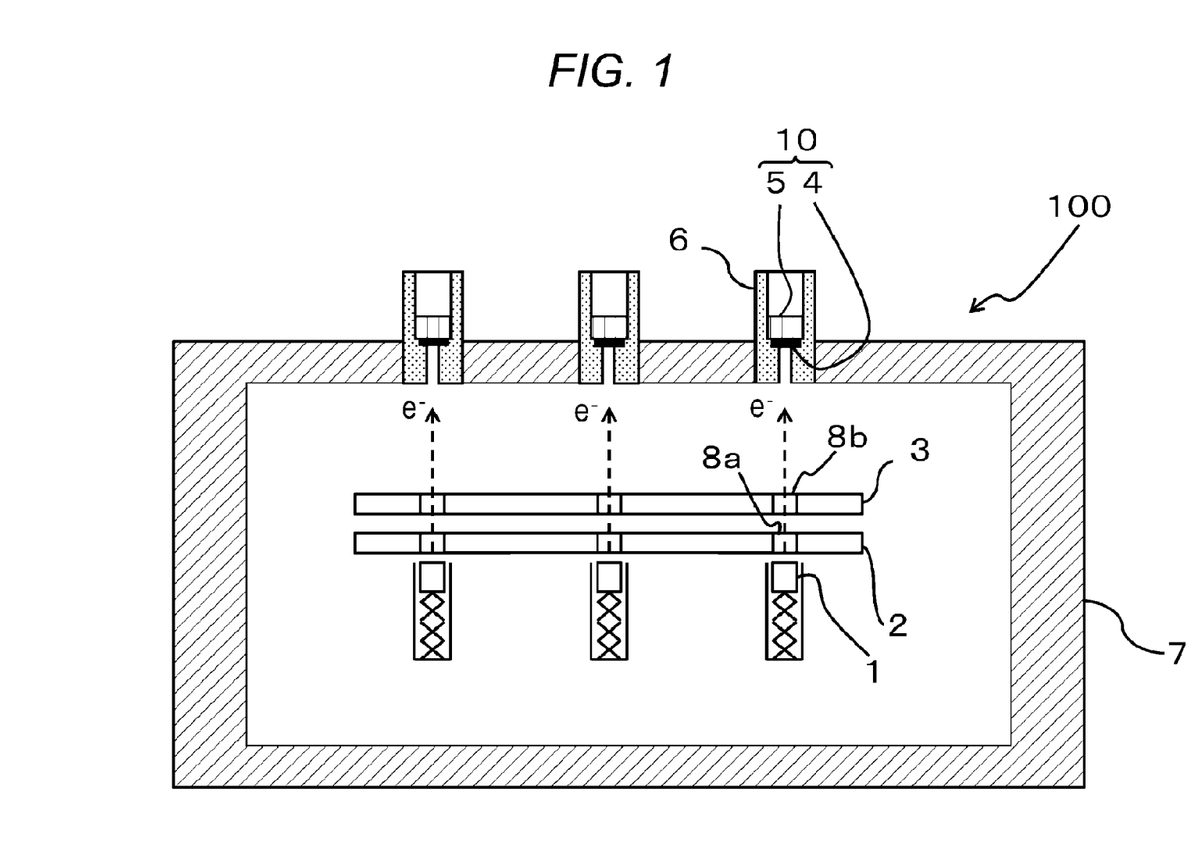
FIG. 1 is a schematic diagram illustrating a constitution of a multi-radiation tube according to an embodiment of the present invention.

An example of a multi-radiation tube (hereinafter referred to as radiation tube) according to the present invention will be described with reference to FIG. 1.

A radiation tube 100 includes a plurality of electron guns that each generates an electron beam $e^-$ and a plurality of targets 10 that each generates radiation by collision of the electron beam.

Each electron gun has an electron source (cathode) 1, an extraction electrode 2 that applies a voltage for drawing electrons from the electron source 1, and an intermediate electrode 3 that applies a voltage for converging the drawn electrons into an electron beam. The electron source 1, the extraction electrode 2, and the intermediate electrode 3 are provided in a vacuum chamber 7. As the electron source 1, a cold-cathode electron source, a hot-cathode electron source, or other similar component is used. Further, an electron source of a liquid metal saturation type, which draws electrons under high temperature conditions created by heating the liquid metal with a heater, can be preferably used in order to stably generate a large-current electron beam. The extraction electrode 2 and the intermediate electrode 3 can be formed of a conductive metal such as molybdenum. The intermediate electrode 3 and the extraction electrode 2 are located between the electron sources 1 and the intermediate electrode 3. More specifically, the extraction electrode 2 is located closer to the electron sources 1 than to the targets 10, and the intermediate electrode 3 is located closer to the extraction electrode 2 than to the targets 10.

Each target 10 includes a supporting substrate 5 formed of a radiation transmissive material and a target layer 4 stacked on the substrate 5. In each target 10, the target layer 4 generates radiation by being irradiated with an electron beam $e^-$ emitted from a corresponding electron source 1. As materials of the supporting substrate 5, low-atomic-number materials including beryllium and diamond are desirable. As materials of the target layer 4, heavy metal materials of atomic numbers of 26 or higher are desirable in terms of efficiency of radiation generation. Specifically, tungsten, molybdenum, chromium, copper, cobalt, iron, rhodium, rhenium, or an alloy material thereof may be used for the target layer 4. Each target 10 is provided in a manner to separate a middle portion of a hollow in a cylindrical supporting board 6 provided at an opening of the vacuum chamber 7, with the target layer 4 facing the corresponding electron source 1. The supporting boards 6 and the targets 10 form a part of the wall surface of the vacuum chamber 7 in a manner that can contribute to maintaining vacuum-tightness of the inside of the vacuum chamber 7.

The extraction electrode 2 and the intermediate electrode 3 have openings 8a and 8b, respectively, for each electron source 1. Electrons emitted from each electron source 1 pass through the corresponding openings 8a and 8b. The extraction electrode 2 is formed of a single electrode material having a plurality of openings 8a and the intermediate electrode 3 is formed of a single electrode material having a plurality of openings 8b. Note that each of the extraction electrode 2 and the intermediate electrode 3 may be divided into electrode pieces corresponding to the electron sources 1, respectively, and that the openings 8a and 8b may be provided in each extraction electrode piece and intermediate electrode piece, respectively.

Figure 2A:
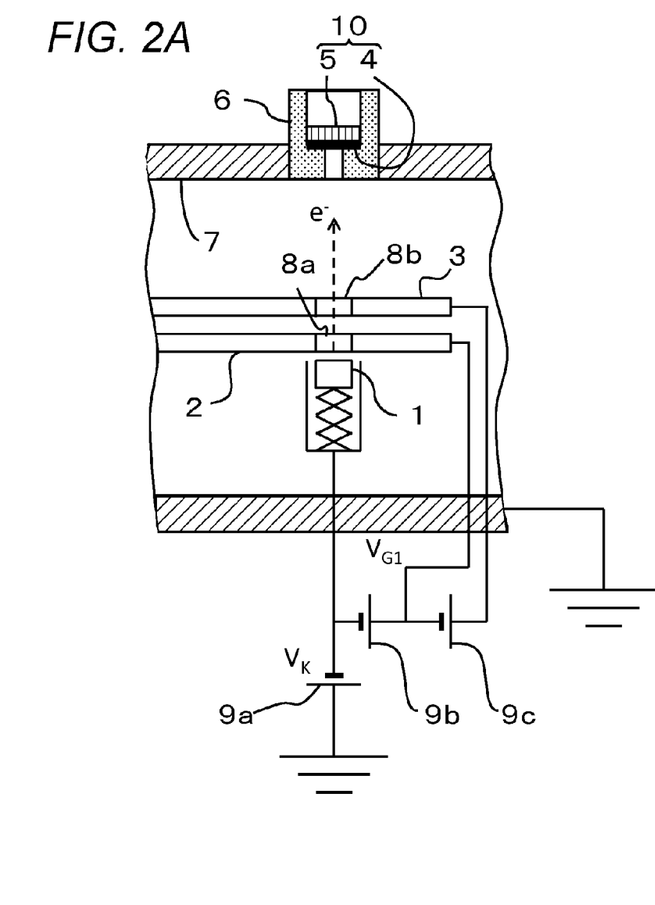
FIG. 2A is a circuit diagram and FIG. 2B is a potential distribution graph illustrating a method for applying a potential to the multi-radiation tube.
Figure 2B:
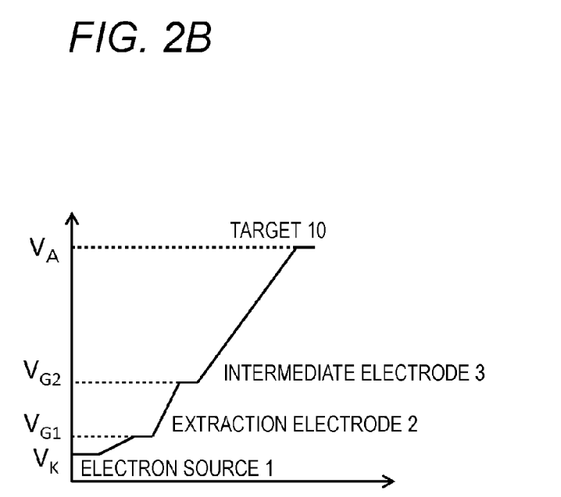

FIG. 2A illustrates an exemplary control circuit used to apply a voltage potential to the components of the radiation tube 100. As illustrated in FIG. 2A, the vacuum chamber 7 and the targets 10 have a ground potential. A voltage source 9a defines the potential difference between the targets 10 and the electron sources 1. A voltage source 9b (extraction electrode potential defining unit) defines the potential of the extraction electrode 2. A voltage source 9c (intermediate electrode potential defining unit) defines the potential of the intermediate electrode 3 together with the voltage source 9b. A negative potential is applied to the electron guns in order to accelerate electrons and make the electron beams collide with the targets 10. As illustrated in FIG. 2B, the electron sources 1, the extraction electrode 2, the intermediate electrode 3, and the targets 10 have potentials $V_K$, $V_{G1}$, $V_{G2}$, and $V_A$, respectively. The relations of these potentials is $V_K \leq V_{G1} \leq V_{G2} \leq V_A$. In one embodiment, the potential differences between the electron sources 1 and the extraction electrode 2 range roughly from 50 V to 500 V. The potential difference between the extraction electrode 2 and the intermediate electrode 3 ranges roughly from 1 kV to 10 kV. The potential differences between the electron sources 1 and the targets 10 range roughly from 10 kV to 150 kV. In other words, in one embodiment, an electron beam drawn from each electron source 1 collides with a respective target layer 4 with an energy of approximately 10 keV to 150 keV so that radiation is generated selectively from each target 10 in a time-divided manner.

The radiation tube 100 has a plurality of radiation focal points (hereinafter referred to as focal points). Radiation is not generated from all of the focal points at one time and is generated from the focal points one by one in a time-division manner. That is, the radiation unit 101 includes a selection circuit that selects a single electron source 1 from the plural electron sources 1, and allows electrons to be emitted from one electron source (the selected electron source 1) at a time. In this manner, an electron beam collides with one focal point alone in a time-division manner.

Figure 3:
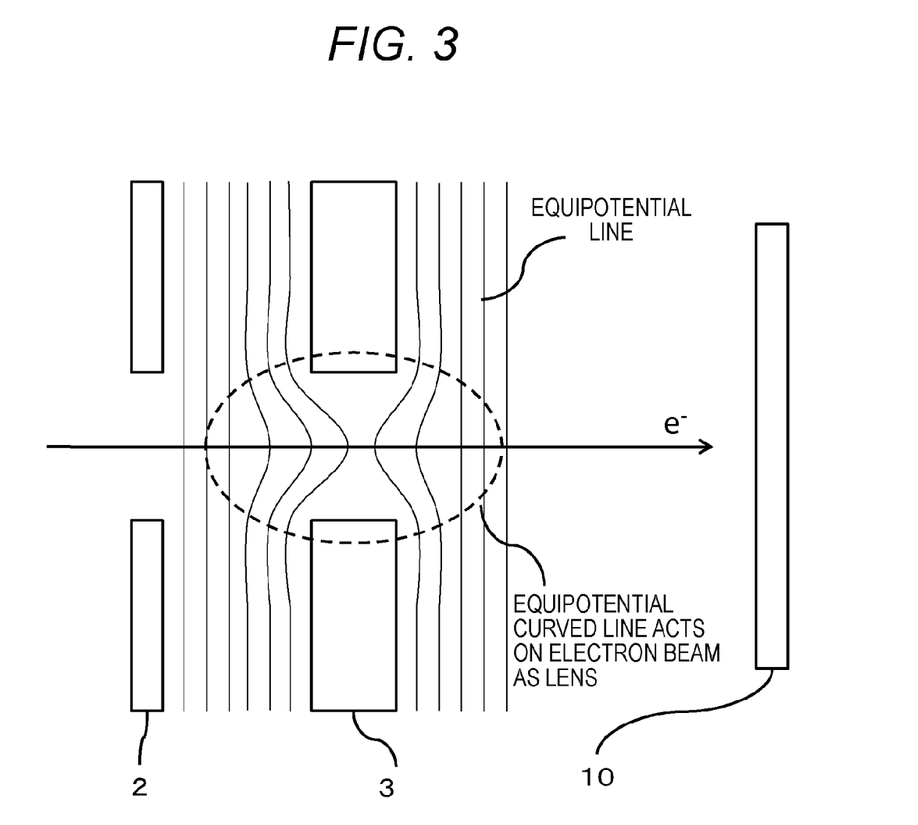
FIG. 3 is an explanatory diagram illustrating an action of a lens, using an equipotential curved line.

As shown in FIG. 3, the intermediate electrode 3 acts as an electrostatic lens on an electron beam. In this manner it is possible to control a state in which the targets 10 are being irradiated with electron beams, by adjusting a distribution of an electric field formed by the intermediate electrode 3. Specifically, it is possible to control the sizes of focal points obtained by collision of the electron beams with the targets 10. The focal point herein represents a radiation generation region, where the target layer 4 of the target 10 is irradiated with electrons. The size of the focal point can be controlled by adjusting the size of the cross section of the electron beam. The size of the cross section of the electron beam (size of electron beam focal point) can be adjusted in a manner that the electric field distribution formed by the intermediate electrode 3 is changed by changing the condition of the electrostatic control for the intermediate electrode 3 acting as an electrostatic lens.

A first method for adjusting the electric field distribution formed by the intermediate electrode 3 is to change a potential to be applied to the intermediate electrode 3. If the potential to be applied to the intermediate electrode 3 is varied with respect to potentials to be applied to the targets 10, the electron sources 1, and the extraction electrode 2, change occurs in the electric field distribution before and after the intermediate electrode 3 with respect to a direction in which the electrons travel, so that the path of an electron beam passing through the electric field is affected. The size of the cross section of the electron beam is accordingly varied so that the size of the focal point can be controlled.

A second method for adjusting the electric field distribution formed by the intermediate electrode 3 is to change the position of the intermediate electrode 3 forward and backward with respect to the direction in which the electrons travel. If the distances between the targets 10 and the intermediate electrode 3 and the distance between the extraction electrode 2 and the intermediate electrode 3 are varied, change occurs in the electric field distribution before and after the intermediate electrode 3 with respect to the direction in which the electrons travel, so that the path of an electron beam passing through the electric field is affected. The size of the cross section of the electron beam is accordingly varied so that the size of the focal point can be controlled.

Figure 4:
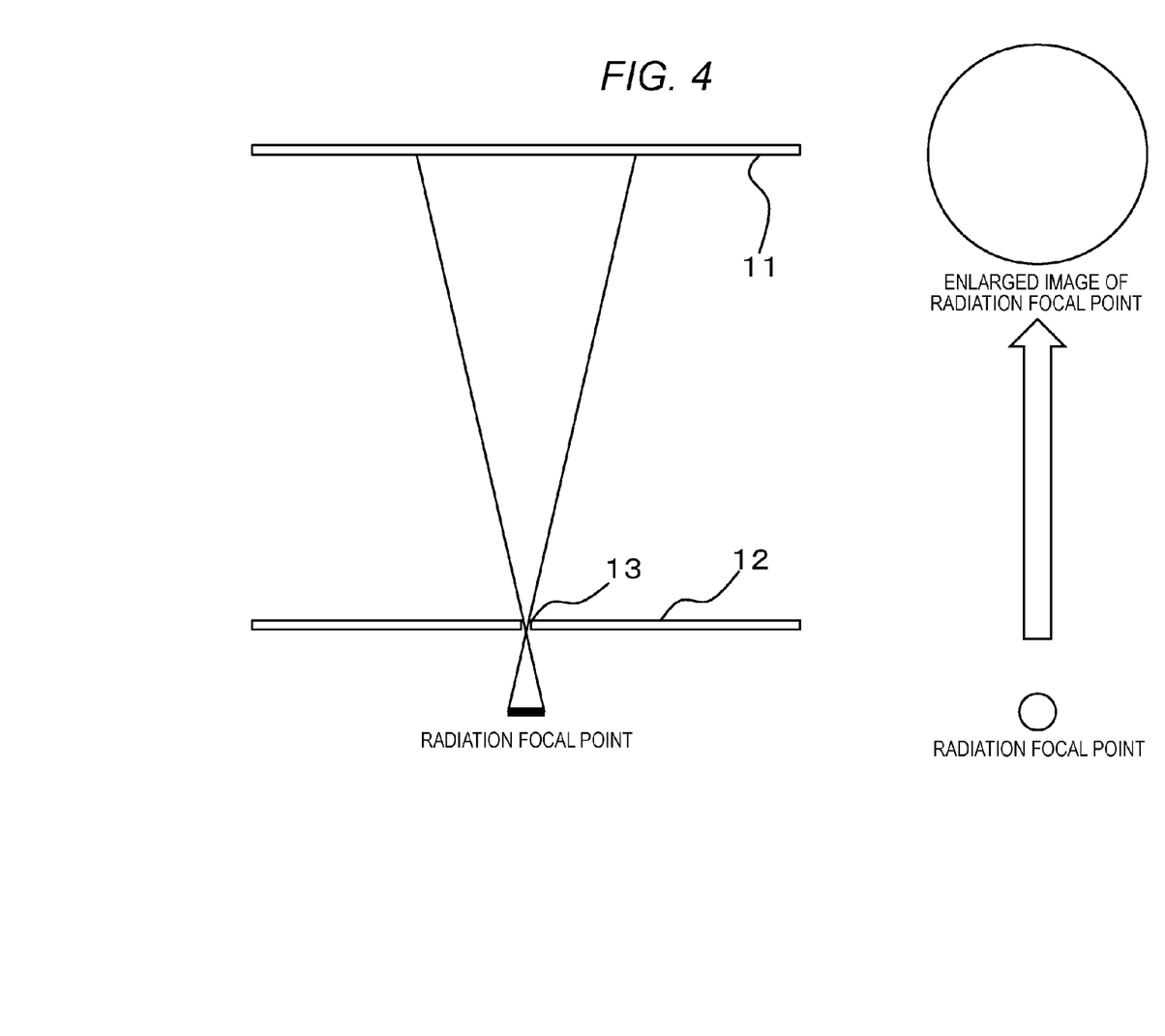
FIG. 4 is an explanatory diagram illustrating a method for measuring the size of a focal point.

A potential condition or a position condition to be provided to the intermediate electrode 3 can be specified from the relation between the potential or the position of the intermediate electrode 3 and the size of the focal point. The relation is established (determined) by measuring the size (diameter) of the focal point while changing the electrostatic control condition to be provided to the intermediate electrode 3. The size of the focal point is measured with a pinhole lens 12 and a radiation image sensor 11, as shown in FIG. 4. The pinhole lens 12 is arranged between the focal point and the radiation image sensor 11. When radiation is emitted from the focal point, an irradiated region of the radiation image sensor 11 which has been irradiated with the radiation has a shape similar to the shape of the focal point having been enlarged and projected. Hence, the size of the focal point can be measured by detecting the irradiated region of the radiation image sensor 11 which has been irradiated with the radiation. With this method, the electrostatic control condition to be provided to the intermediate electrode 3 and the size of the focal point are correlated with each other for each electron source 1, and the correlations are stored in a storage unit M. The electrostatic control condition of the intermediate electrode 3 can be controlled to an appropriate one in a manner that when the radiation tube 100 is to be driven by emitting electrons from a selected electron source 1 selected by the selection circuit, the electrostatic control condition (which has been previously stored) is read out from a storage unit M for the selected electron source 1. In other words, providing the intermediate electrode 3 with pre-established electrostatic control conditions for each electron source 1 to be driven permits the size of an electron beam focal point to be controlled (e.g., kept constant or adjusted) according to the selected electron source. In this manner, any one of the electron sources 1 is driven independently to emit an electron beam with an appropriate focal point size.

Setting of the electrostatic control condition and control based on the set condition will be described more specifically.

An example (Example 1) will be described in which the size of each focal point is controlled in a manner that when radiation is sequentially generated from three targets 10, respective potential conditions to be provided to the intermediate electrode 3 during driving of the three targets 10 are varied. Herein, the respective numbers of the targets 10 and the electron sources 1 are three, and the targets 10 and the electron sources 1 are provided in one-to-one correspondence. Further, the respective numbers of the extraction electrode 2 and the intermediate electrode 3 is one, and the extraction electrode 2 and the intermediate electrode 3 act on all the electrons from the three electron sources 1.

The potential conditions to be provided to the electron sources 1, the extraction electrode 2, and the intermediate electrode 3 when the targets 10 have a ground potential are determined beforehand. In order to determine the above conditions, the size of the focal point is measured using the pinhole lens 12 and the radiation image sensor 11 as shown in FIG. 4 while the potential conditions are being changed. The combinations of the obtained potential conditions are stored in the storage unit (memory). The measurement can be performed under such potential conditions that the potential differences between the electron sources 1 and the targets 10 are fixed within the range of approximately 10 kV to 150 kV and the targets 10 are grounded.

An example of measuring the size of the focal point will be described with reference to FIG. 4.

In order to determine the radiation intensity first, the current amount of an electron beam is set to a required value by changing the potential differences between the electron sources 1 and the extraction electrode 2. For example, when the required current ranges roughly from 5 mA to 30 mA, the potential differences between the electron sources 1 and the extraction electrode 2 can be set within the range from approximately 50 V to 500 V depending on the configuration or the size of the radiation tube 100.

Next, the size of a focal point is determined. A focal point size is measured in a manner that the potential to be provided to the intermediate electrode 3 is changed with respect to the previously determined potential differences between the electron sources 1 and the extraction electrode 2 and resultant radiation is passed through the pinhole lens 12 to be projected to the radiation image sensor 11. An enlarged image of a focal point measured by the radiation image sensor 11 is similar in shape to the focal point. The similarity ratio is equal to the ratio of the distance between the targets 10 and a pinhole 13 of the pinhole lens 12 and the distance between the pinhole 13 and the radiation image sensor 11. Hence, the size of a focal point is known from an enlarged image of the focal point measured by the radiation image sensor 11. Specifically, when the required size (diameter) of a focal point is set to be within the range from approximately 0.2 mm to 1 mm, the potential differences between the intermediate electrode 3 and the electron sources 1 are set to be within the range from approximately 1 kV to 10 kV, and the potential condition to be provided to the intermediate electrode 3 and the potential conditions to be provided to the electron sources 1 and the extraction electrode 2 are stored in the storage unit M.

An electron source 1 corresponding to a target 10 is selected by the selection circuit and is driven so that an electron beam is drawn from the electron source 1, whereby radiation can be generated from the target 10. In this case, no radiation is generated from the other targets 10.

Figure 5:
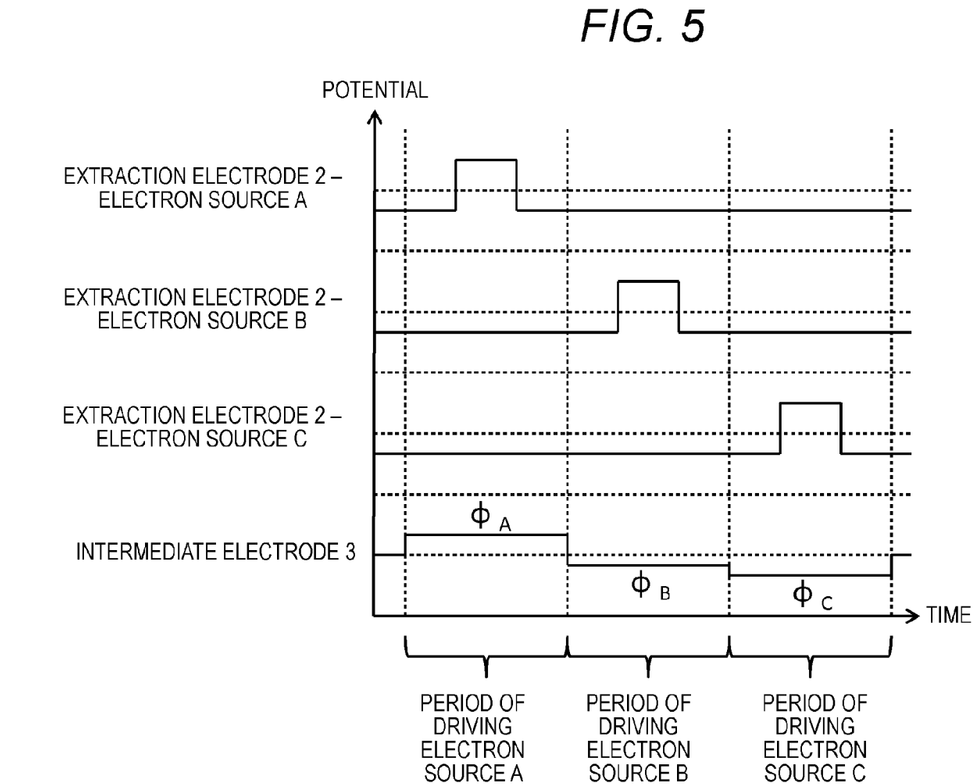
FIG. 5 is a time chart illustrating relations between the potential of an intermediate electrode and respective potential differences between electron sources and an extraction electrode.

A method for applying a potential will be described with reference to a time chart shown in FIG. 5. In FIG. 5, electron sources A to C are used as three electron sources. A potential to be provided to each of the electron sources 1 corresponding to the targets 10 from which radiation is not to be generated is made larger than a potential to be provided to the extraction electrode 2. No electron beam is thus output. In a period of driving the electron source A, a potential to be provided to the extraction electrode 2 is made smaller than potentials to be provided to the electron sources B and C. A potential to be provided to the electron source 1 corresponding to the target 10 from which radiation is to be generated is made smaller than the potential to be provided to the extraction electrode 2. An electron beam is thus drawn. In the period of driving the electron source A, the potential to be provided to the extraction electrode 2 is made larger than the potential to be provided to the electron source A.

Figure 6:
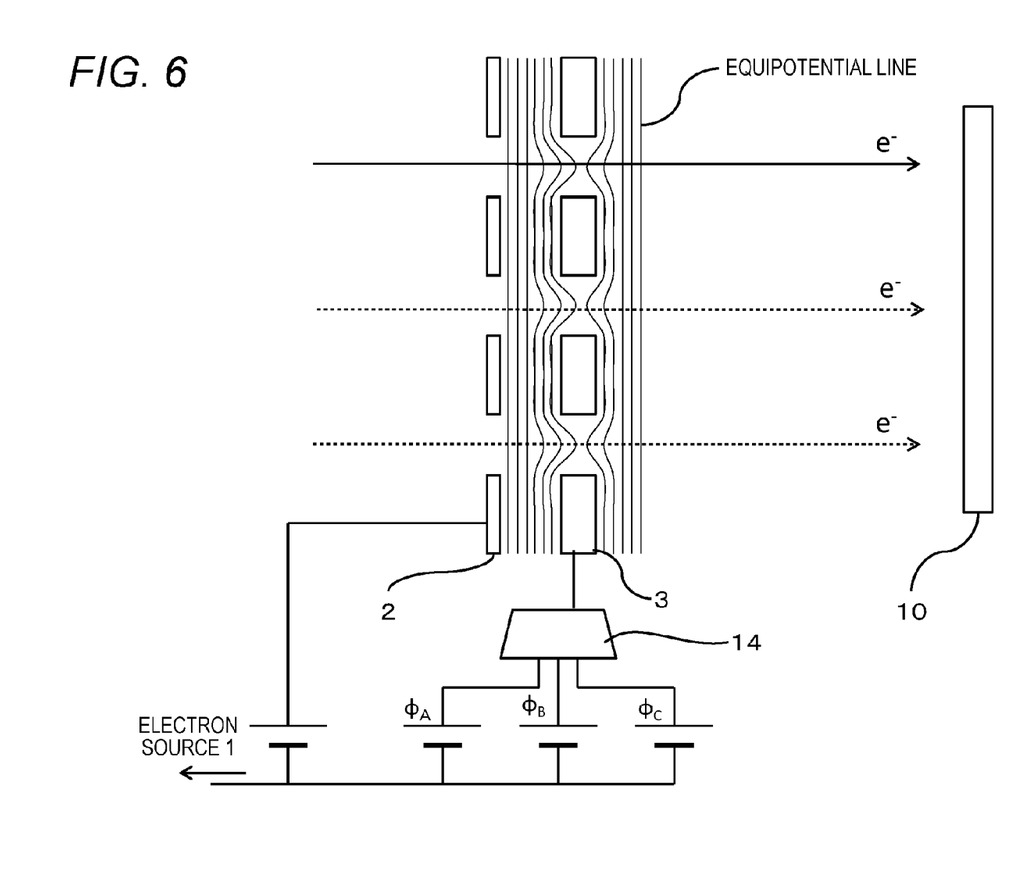
FIG. 6 is an explanatory diagram illustrating a switching circuit.

Although the intermediate electrode 3 acts on all of the three electron sources 1, the intermediate electrode is provided with a potential condition alone which satisfies an emitting condition of an electron beam for a specific electron source 1 from which the electron beam is generated. Specifically, when an electron beam is emitted from the electron source A, an intermediate electrode potential $\phi_A$ is provided. When an electron beam is emitted from the electron source B or C, an intermediate electrode potential $\phi_B$ or $\phi_C$ is provided, respectively. A changing unit changes the electrostatic control condition of the intermediate electrode 3. As the changing unit, a switching circuit 14 is used as shown in FIG. 6. With the switching circuit 14, the intermediate electrode potential is switched in accordance with switching of driving of the electron sources 1. When the three electron sources 1 are driven one by one in a time-division manner, the intermediate electrode potentials corresponding to the electron sources 1, respectively, can be provided and the characteristic of each electron beam can be suitably adjusted.

Second Embodiment

Next, an example (Example 2) will be described in which the size of each focal point is controlled in such a manner that radiation is sequentially generated from the targets 10 and a potion condition to be provided to the intermediate electrode 3 is changed while each of the targets 10 is being driven. The targets 10 and the electron sources 1 are the same in number and are provided in one-to-one correspondence. The respective numbers of the extraction electrode 2 and the intermediate electrode 3 are one, and the extraction electrode 2 and the intermediate electrode 3 act on all of the electron sources 1. The constitution of the radiation tube 100 and a method for measuring the focal point size are the same as in the first embodiment.

In the embodiment, the focal point diameter is adjusted by changing the position of the intermediate electrode. As in the first embodiment, the potential difference between each electron source 1 and the extraction electrode 2 is changed so that the current amount of an electron beam is adjusted to a required value. Further, the position of the intermediate electrode 3 is changed under the above condition, and the size of a resultant focal point is measured. The method for measuring the focal point size is as described above. The position information of the intermediate electrode 3 when a required focal point size can be obtained is stored in a storage device. As an example of position change of the intermediate electrode 3, when the thickness of the intermediate electrode 3 is set to be within the range from approximately 1 mm to 5 mm, the distances of the intermediate electrode 3 to the targets 10 can be varied within the range from approximately 5 mm to 50 mm and the distance of the intermediate electrode 3 to the extraction electrode 2 can be varied within the range from approximately 1 mm to 10 mm.

An electron beam is drawn from a single electron source 1 alone which corresponds to a single target 10, so that radiation can be generated from the target 10. Potentials to be provided to the electron sources 1 and the extraction electrode 2 are the same as in the first embodiment.

Figure 7:
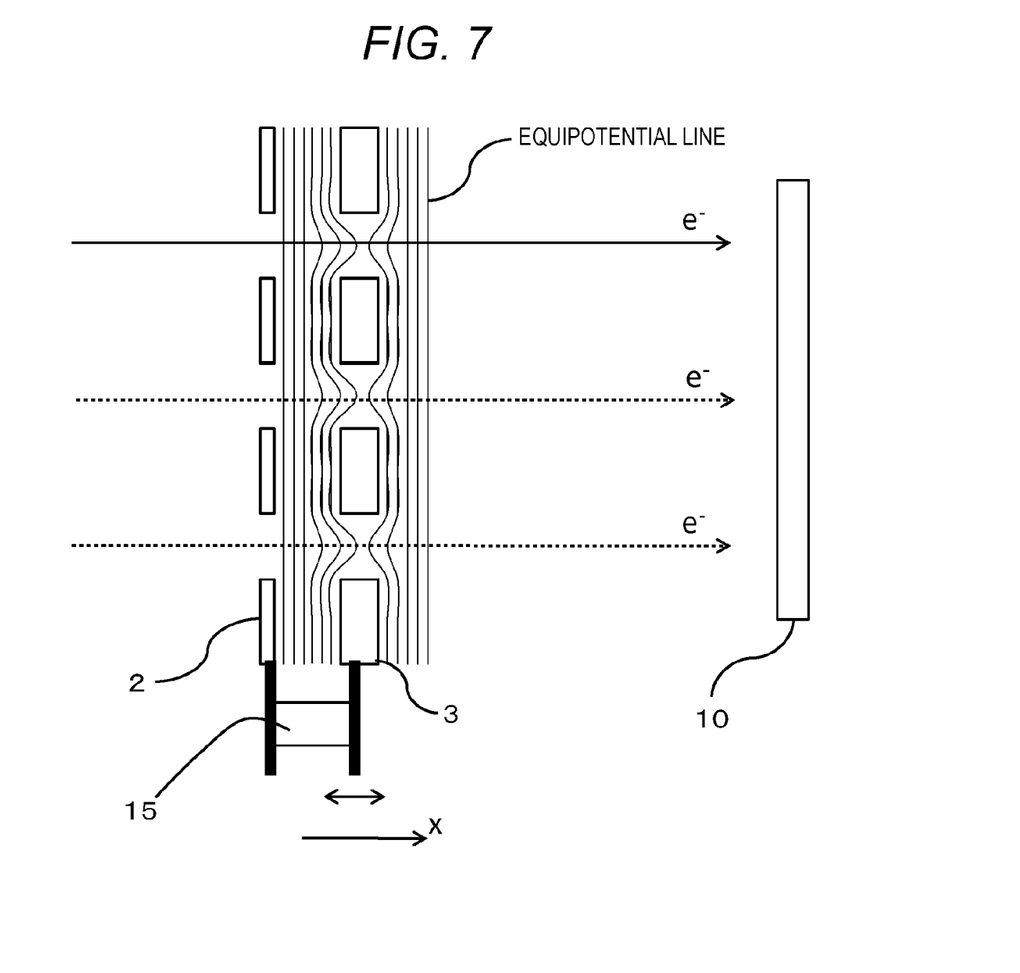
FIG. 7 is an explanatory diagram illustrating a piezoelectric element.
Figure 8:
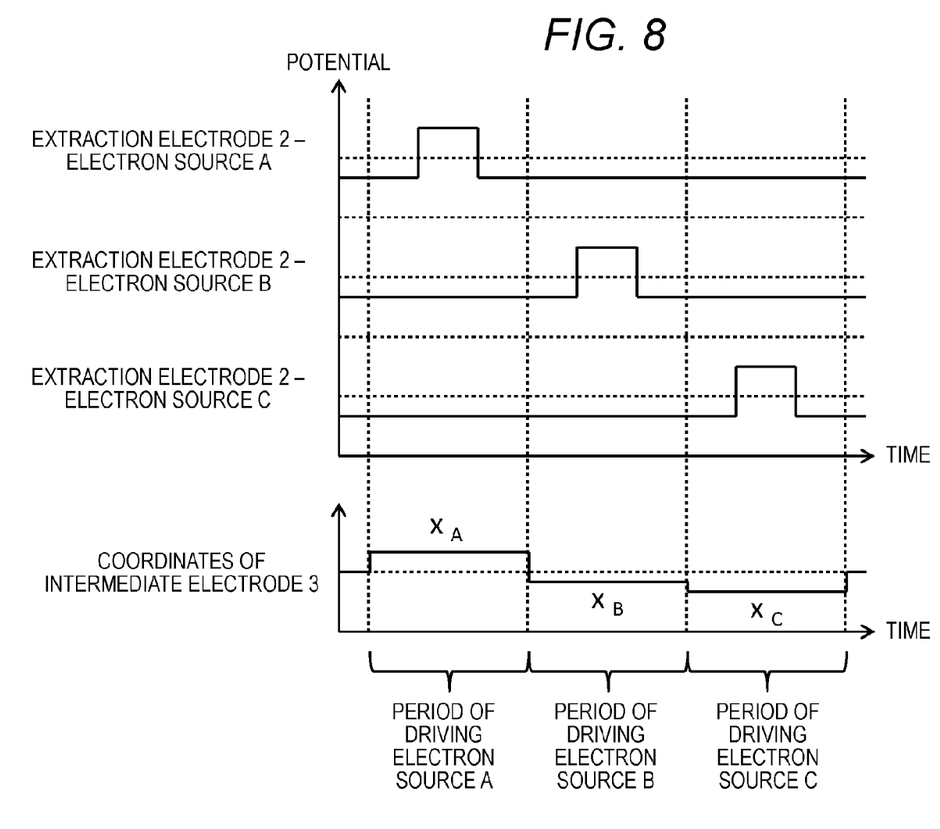
FIG. 8 is a time chart illustrating relations between the position of the intermediate electrode and the respective potential differences between the electron sources and the extraction electrode.

The position of the intermediate electrode 3 is changed in order to control the diameter of an electron beam which collides with a target 10. The position information at that time is read from a storage unit M. As a changing unit for changing the position of the intermediate electrode 3, a piezoelectric element 15 shown in FIG. 7 may be used. The piezoelectric element 15 expands and compresses in a direction (X direction) parallel to a path of the electron beams e⁻ (a direction in which the electrons travel), and moves the intermediate electrode 3 along that direction. A relative position of the intermediate electrode 3 and the extraction electrode 2 is moved accordingly. Although the intermediate electrode 3 acts on all of the electron sources 1, the position of the intermediate electrode 3 is determined so that an emitting condition is satisfied of an electron beam for a specific electron source 1 from which the electron beam is drawn. That is, as shown in FIG. 8, when an electron beam is emitted from the electron source A, a position $X_A$ is provided to the intermediate electrode 3. When the electron beam is emitted from the electron source B or C, a position $X_B$ or $X_C$ is provided to the intermediate electrode 3, respectively. In this way, when the plurality of electron sources 1 are sequentially driven one by one in a time-division manner, the position of the intermediate electrode 3 is determined according to each electron source 1. Further, the size of the focal point is adjusted according to each electron source 1.

Third Embodiment

Figure 9:
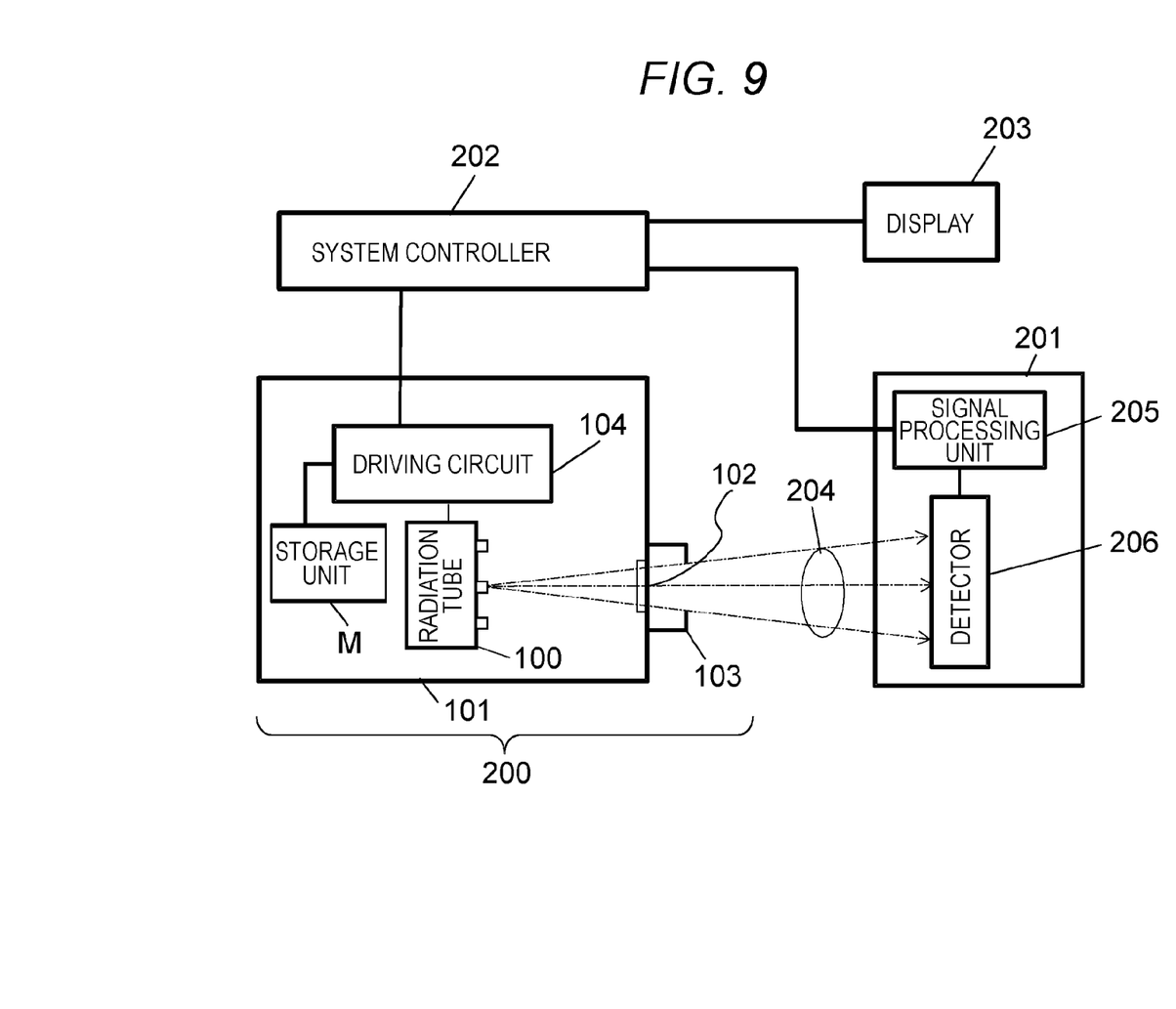
FIG. 9 is a diagram illustrating an exemplary configuration of a radiation imaging system according to the present invention.

FIG. 9 is a configuration diagram illustrating a radiation imaging system according to the present invention. The radiation tube 100 is the same as described in the first or second embodiments. A radiation generation unit 101 contains the radiation tube 100 and a driving circuit 104 that controls the operation of the radiation tube 100. Radiation having generated in the radiation tube 100 is emitted from a radiation transmissive window 102 of the radiation generation unit 101 to the outside. The radiation generation unit 101 and a movable diaphragm unit 103 provided at the radiation transmissive window 16 form a radiation generator 200. The movable diaphragm unit 103 has a function of adjusting the width of the irradiation field of the radiation emitted from the radiation generation unit 101. Further, the movable diaphragm unit 103 may additionally have a function of displaying the irradiation field of the radiation simulated with visible light.

A system controller 202 controls the radiation tube 100 of the radiation generator 200 and a radiation detector 201 in conjunction with each other. The driving circuit 104 outputs control signals to a radiation tube 100 under the control of the system controller 202. The control signals control the emission state of the radiation emitted from the radiation generator 200. The radiation emitted from the radiation generator 200 goes through an object 204, and is detected by a detector 206. The detector 206 converts the detected radiation to an image signal and outputs the converted signal to a signal processing unit 205. The signal processing unit 205 performs predetermined signal processing on the image signal under the control of the system controller 202, and outputs the processed image signal to the system controller 202. The system controller 202 outputs, to a display 203, a display signal for allowing the display 203 to display an image based on the processed image signal. The display 203 displays the image based on the display signal on a screen as a captured image of the object 204. A representative example of the radiation is X-ray radiation. The radiation generation unit 101 and the radiation imaging system according to the present invention can be used as an X-ray generation unit and an X-ray imaging system, respectively. The X-ray imaging system can be used for non-destructive inspection of industrial products or pathological diagnosis of human bodies and animals.

According to the present invention, sequential change of the electrostatic control condition of the intermediate electrode makes it possible to achieve, in a case where any one of the electron sources is selected, substantial uniformity in the size of a region of a target which is irradiated with electrons. Hence, it is possible to keep the intensity distribution of radiation emitted from the multi-radiation tube substantially constant. The radiation imaging system using the radiation tube according to the present invention advantageously provides improved image quality of a captured image.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-248965, filed Nov. 13, 2012, which is hereby incorporated by reference herein in its entirety.

What is claimed is:
1. A multi-radiation unit, comprising:
(a) a multi-radiation tube including
a plurality of electron sources,
a plurality of targets respectively corresponding to the plurality of electron sources and
an intermediate electrode located between the electron sources and the targets, the intermediate electrode including openings through which electrons emitted from the electron sources pass through;
(b) a selection circuit configured to allow electrons to be emitted from a selected electron source selected from the plurality of electron sources;
(c) an intermediate electrode potential defining unit configured to define a potential of the intermediate electrode;
(d) a storage unit configured to store, for each of the plurality of electron sources, an electrostatic control condition of the intermediate electrode for obtaining a predetermined irradiated state of a target corresponding to the selected electron source; and
(e) a changing unit configured to change, when electrons are emitted from the selected electron source, the electrostatic control condition of the intermediate electrode based on the electrostatic control condition stored in the storage unit for the selected electron source.

2. The multi-radiation unit according to claim 1, wherein the electrostatic control condition of the intermediate electrode is a condition in which a size of an electron beam focal point is fixed when electrons from the selected electron source are emitted.

3. The multi-radiation unit according to claim 1, wherein the electrostatic control condition of the intermediate electrode is a potential to be applied to the intermediate electrode.

4. The multi-radiation unit according to claim 3, wherein the changing unit is a switching circuit for switching the potential to be applied to the intermediate electrode.

5. The multi-radiation unit according to claim 1, wherein the electrostatic control condition of the intermediate electrode is a condition to set a distance between the intermediate electrode and the electron sources.

6. The multi-radiation unit according to claim 5, wherein the changing unit is a piezoelectric element for changing the distance between the intermediate electrode and the electron sources.

7. A radiation imaging system, comprising:
   a multi-radiation unit including
      (a) a multi-radiation tube which having
         a plurality of electron sources,
         a plurality of targets respectively corresponding to the plurality of electron sources and
         an intermediate electrode located between the electron sources and the targets, the intermediate electrode including openings through which electrons emitted from the electron sources pass through,
      (b) a selection circuit configured to allow electrons to be emitted from a selected electron source selected from the plurality of electron sources,
      (c) an intermediate electrode potential defining unit configured to define a potential of the intermediate electrode,
      (d) a storage unit configured to store, for each of the plurality of electron sources, an electrostatic control condition of the intermediate electrode for obtaining a predetermined irradiated state of a target corresponding to the selected electron source, and
      (e) a changing unit configured to change, when electrons are emitted from the selected electron source, the electrostatic control condition of the intermediate electrode based on the electrostatic control condition stored in the storage unit for the selected electron source;
   a radiation detector configured to detect radiation having been emitted from the multi-radiation tube and having passed through an object; and
   a controller configured to control the multi-radiation tube and the radiation detector in conjunction with each other.

* * * * *